(12) United States Patent
Becker et al.

(10) Patent No.: US 11,333,320 B2
(45) Date of Patent: May 17, 2022

(54) RETROREFLECTOR LED SPECTRUM ENHANCEMENT METHOD AND APPARATUS

(71) Applicant: American Sterilizer Company, Mentor, OH (US)

(72) Inventors: Aaron James Becker, Willoughby, OH (US); David Jesurun, South Euclid, OH (US)

(73) Assignee: American Sterilizer Company, Mentor, OH (US)

( * ) Notice: Subject to any disclaimer, the term of this patent is extended or adjusted under 35 U.S.C. 154(b) by 0 days.

(21) Appl. No.: 16/570,199

(22) Filed: Sep. 13, 2019

(65) Prior Publication Data
US 2020/0124250 A1 Apr. 23, 2020

Related U.S. Application Data

(60) Provisional application No. 62/748,697, filed on Oct. 22, 2018.

(51) Int. Cl.
  *F21V 7/04* (2006.01)
  *F21V 9/30* (2018.01)
  (Continued)

(52) U.S. Cl.
  CPC ............. *F21V 7/04* (2013.01); *F21V 9/30* (2018.02); *F21W 2131/205* (2013.01); *F21Y 2115/10* (2016.08)

(58) Field of Classification Search
  CPC . F21V 7/04; F21V 9/30; F21V 19/001; F21V 13/04; F21V 5/04; F21V 7/0091;
  (Continued)

(56) References Cited

U.S. PATENT DOCUMENTS 6,252,638 B1 * 6/2001 Johnson .............. G02F 1/13471
349/5
6,312,144 B1 11/2001 Li
(Continued)

FOREIGN PATENT DOCUMENTS

CN 206786577 U * 12/2017 .............. F21V 19/00
EP 1081771 A2 3/2001
(Continued)

OTHER PUBLICATIONS

Machine English Translation of CN206786577U, Fang Xienfeng (Year: 2017).*

(Continued)

*Primary Examiner* — Rajarshi Chakraborty
*Assistant Examiner* — Glenn D Zimmerman
(74) *Attorney, Agent, or Firm* — Kusner & Jaffe

(57) ABSTRACT

A method and apparatus for improving the optical properties of an LED using a retroreflector element. A light emitting apparatus includes a substrate, at least one light emitting device attached to the substrate and including an outer primary light emitting surface through which substantially all light is emitted, and a retroreflector assembly attached to the substrate. The retroreflector assembly includes a proximal surface adjacent to the substrate, a distal surface spaced away from the substrate, and a retroreflective portion arranged between proximal surface and the distal surface. A distance from the distal surface to the substrate is less than or equal to a distance from the outer primary light emitting surface to the substrate.

32 Claims, 6 Drawing Sheets

(51) Int. Cl.
  *F21W 131/205* (2006.01)
  *F21Y 115/10* (2016.01)
(58) Field of Classification Search
  CPC ......... F21W 2131/205; F21W 2131/20; F21Y
    2115/10; H01L 33/00; H01L 2933/0058;
    H01L 33/50; H01L 33/60; A61B
    2090/308; A61B 2090/309; A61B 1/06;
    A61B 1/0638; A61B 1/0653; A61B
    1/0692; A61B 90/30; A61B 1/0684; F21K
    9/60; G02B 19/0028; G02B 19/0061;
    H05B 33/00; H05B 33/22
  See application file for complete search history.

(56) References Cited

U.S. PATENT DOCUMENTS

| | | | |
|---|---|---|---|
| 6,353,489 B1 | 3/2002 | Popovich et al. | |
| 6,739,734 B1 | 5/2004 | Hulgan | |
| 7,025,486 B2 | 4/2006 | Lang et al. | |
| 7,445,340 B2 | 11/2008 | Conner et al. | |
| 7,450,799 B2 | 11/2008 | Selbrede et al. | |
| 7,631,991 B2 | 12/2009 | Anderson et al. | |
| 7,687,815 B2 | 3/2010 | Kim | |
| 7,874,704 B2 | 1/2011 | Falicoff et al. | |
| 8,097,894 B2 | 1/2012 | Bierhuizen et al. | |
| 8,274,220 B2 | 9/2012 | Destain et al. | |
| 8,388,190 B2 | 3/2013 | Li et al. | |
| 8,727,573 B2 | 5/2014 | Holder | |
| 9,574,746 B2 | 2/2017 | Broughton | |
| 9,761,753 B2 | 9/2017 | Nakabayashi | |
| 9,797,567 B2 | 10/2017 | Kastner-Jung et al. | |
| 2002/0089857 A1* | 7/2002 | Borders | F21V 21/403 362/399 |
| 2006/0105485 A1* | 5/2006 | Basin | G02B 19/0028 438/27 |
| 2008/0291682 A1 | 11/2008 | Falicoff et al. | |
| 2009/0112196 A1 | 4/2009 | Rabiner | |
| 2009/0115313 A1* | 5/2009 | Lu | H01L 33/505 313/503 |
| 2009/0128921 A1* | 5/2009 | Roth | G02B 19/0028 359/641 |
| 2009/0152573 A1 | 6/2009 | Loh et al. | |
| 2009/0273918 A1 | 11/2009 | Falicoff et al. | |
| 2011/0310605 A1* | 12/2011 | Renn | F21V 19/0035 362/235 |
| 2012/0188772 A1* | 7/2012 | Sakai | H01L 33/505 362/296.01 |
| 2013/0070461 A1 | 3/2013 | Pickard | |
| 2014/0231846 A1 | 8/2014 | Lin | |
| 2014/0346533 A1* | 11/2014 | Andrews | H01L 33/08 257/88 |
| 2015/0129910 A1* | 5/2015 | Sekowski | H05K 1/00 257/91 |
| 2017/0126944 A1 | 5/2017 | Jagt et al. | |
| 2018/0066827 A1* | 3/2018 | Joergensen | F21K 9/62 |
| 2018/0188772 A1* | 7/2018 | Lee | H01Q 1/22 |
| 2018/0315901 A1* | 11/2018 | Lopez | H01L 33/58 |
| 2019/0326485 A1* | 10/2019 | Damborsky | H01L 33/26 |
| 2020/0140312 A1* | 5/2020 | Yokota | C03C 3/087 |

FOREIGN PATENT DOCUMENTS

| | | | |
|---|---|---|---|
| JP | 2004232387 A | * | 8/2004 |
| JP | 2013-222646 A | | 10/2013 |

OTHER PUBLICATIONS

Machine English Translation of CN206786577U created from Dialog, Fang, Dec. 22, 2017 (Year: 2017).*
International Search Report and Written Opinion from corresponding International Patent Application No. PCT/US2019/051216, dated Apr. 3, 2020.
International Search Report from corresponding International Patent Application No. PCT/US2019/051216, dated Jan. 3, 2020.
Cree, "Optimizing PCB Thermal Performance for Cree® XLamp® LEDs," Product Design Guide, www.cree.com/xlamp, 2010-2018.
Website print out of "LEDs: Understanding Optical Performance," A•L Architectural Lighting, www/archlighting.com/technology/leds-understanding-optical-performance_o, print out date, Jul. 6, 2018.
Website print out of "Retroreflector Selector," PLX Innovative Optical Systems, www.plxinc.com/retroreflector-selector, print out date, Apr. 5, 2018.

* cited by examiner

RETROREFLECTOR LED SPECTRUM ENHANCEMENT METHOD AND APPARATUS

RELATED APPLICATION DATA

This application claims the priority of U.S. Provisional Application No. 62/748,697, filed on Oct. 22, 2018, which is hereby incorporated by reference in its entirety.

FIELD OF THE INVENTION

The present invention relates generally to the field of lighting, and more particularly to a method and apparatus for improving the optical properties of an LED using a retroreflector element.

BACKGROUND OF THE INVENTION

Conventional lightheads used for surgical lighting are generally comprised of one or more lighting modules located within a housing. Each lighting module typically includes a plurality of individual light emitting devices, such as LED packages or the like, mounted on a circuit board substrate. It has been observed that certain LEDs project extraneous light emissions in a lateral direction (i.e., to the lateral sides of the LED) and in a rearward direction (i.e., away from the forward facing direction of the LED).

It is often necessary to allow sufficient spacing between LEDs mounted on the circuit board substrate so that the light directed to the lateral sides and rear of the LED does not illuminate the phosphor of an LED located in close proximity. If the light from an LED enters proximate LEDs, then an unintended lighting effect may be observed, such as a change in the chromaticity of the light. Another unintended light effect that may be observed is a halo effect due to the side and rearward light being reflected by the surface of the circuit board substrate and entering the collimator from an apparently larger light source. An apparent larger light source size requires a larger collimator to provide the desired light beam size or concessions on the minimum light beam size a given collimator can produce.

It is further noted that the flux of the forward-directed light produced by such LED is less than the total flux produced by the LED, since a small amount of flux is lost to the side and rearward light.

Another design problem is that the side and rearward light is usually captured in the total lumens specified by an LED manufacturer, since they typically use an integrating sphere that captures all of the light produced by the LED in all directions. Unless the use of the LED in the OEM's design captures the extraneous side and rearward flux, which is very difficult to do, the OEM's design must consider that the rated source lumens will not be observed in the total lumen output of a lighthead. Accordingly, the lighthead's overall beam efficacy (Lumens/Watt) is lowered due to the side and rearward light emissions.

Another problem arises if LEDs with these extraneous light emissions are located too close together on the circuit board substrate of the lighting module. In this case light from neighboring LEDs may enter the phosphor of another (e.g., adjacent) LED, which increases the portion of the light that undergoes a phosphor conversion thus changing the correlated color temperature (CCT) and color. This effect can be so large that only 4 LEDs placed less than 1 mm apart can change the desired color of the light source by seven McAdam's ellipses. This is seven times larger than a human eye can differentiate and is the limit of acceptability of even the least expensive low-quality light sources.

There is a need to adapt certain types of light emitting devices to prevent extraneous light emissions in the lateral side and rearward directions. The present invention provides a method and apparatus that uses a retroreflector element to overcome the drawbacks of prior art light emitting devices having such extraneous light emissions.

SUMMARY OF THE INVENTION

In accordance with the present invention, there is provided a lighting apparatus having improved optical illumination properties, said apparatus comprising a retroreflector element.

In accordance with another aspect of the present invention, there is provided a method for improving the optical illumination properties of a lighting apparatus using a retroreflector element.

According to one aspect of the invention, a light emitting apparatus includes: a substrate; at least one light emitting device attached to the substrate and including an outer primary light emitting surface through which substantially all light is emitted; and a retroreflector assembly attached to the substrate, the retroreflector assembly including a proximal surface adjacent to the substrate, a distal surface spaced away from the substrate, and a retroreflective portion arranged between proximal surface and the distal surface, wherein a distance from the distal surface to the substrate is less than or equal to a distance from the outer primary light emitting surface to the substrate.

In one embodiment, the retroreflector assembly is arranged along lateral sides of the outer primary light emitting surface.

In one embodiment, the distal surface is coplanar with the outer primary light emitting surface.

In one embodiment, at least some extraneous light is emitted through a surface of the light emitting device other than the outer primary light emitting surface, and the retroreflector assembly is configured to reflect the at least some extraneous light back toward the light emitting device.

In one embodiment, the reflected light is directed back onto the at least one light emitting device.

In one embodiment, substantially all light is emitted in a forward-facing direction of the light emitting apparatus, and at least some light is emitted in at least one of i) a lateral direction relative to the forward-facing direction or ii) a reverse-facing direction relative to the forward-facing direction.

In one embodiment, at least some light is emitted in a direction generally orthogonal to the forward-facing direction or a direction generally opposite the forward-facing direction.

In one embodiment, an intensity of the extraneous light is substantially unaltered over an optical path between the at least one light emitting device and the retroreflector assembly.

In one embodiment, the light emitting apparatus includez an optical component having at least one of refractive or reflective portions arranged over the at least one light emitting device, the optical component configured to collimate light emitted by the outer primary light emitting surface.

In one embodiment, the at least one light emitting device is arranged between the substrate and the optical element.

In one embodiment, the retroreflector assembly is indirectly attached to the substrate.

In one embodiment, the collimator is directly attached to the substrate and the retroreflector assembly is attached to the collimator.

In one embodiment, the light emitting device includes a light emitting diode (LED).

In one embodiment, the light emitting device includes a phosphor layer arranged over an output surface of the LED.

In one embodiment, light reflected by the retroreflector assembly includes blue light and white light, the blue light being absorbed by the phosphor layer and reemitted as white light, and white light being diffusely reflected by the phosphor layer.

In one embodiment, the light emitting device includes an encapsulant arranged over the LED, the encapsulant defining the outer primary light emitting surface and a secondary light emitting surface that emits the extraneous light.

In one embodiment, the retroreflective portion spans from the distal surface to the proximal surface.

In one embodiment, the retroreflective portion of the retroreflector assembly is arranged parallel to a lateral side of the light emitting device.

In one embodiment, the retroreflector assembly includes a support member having an inner surface, and a retroreflector arranged on the inner surface.

In one embodiment, the inner surface includes a plurality of walls that define a volume, and the light emitting device is arranged within the volume.

In one embodiment, the substrate includes a planar surface.

In one embodiment, wherein the light emitting apparatus includes a colored filter configured to selectively control a color of reflected light to enhance a spectrum of the light emitted by the light emitting device.

In one embodiment, the at least one light emitting device and a retroreflector of the retroreflector assembly are closely coupled.

According to another aspect of the invention, a surgical light head includes a housing; and a light emitting apparatus as described herein.

In one embodiment, the surgical light head includes a handle for positioning the lighthead, the handle attached to the housing.

According to another aspect of the invention, a method for improving optical illumination properties of a lighting apparatus includes: attaching a light emitting device to a substrate, the light emitting device having an outer primary light emitting surface through which substantially all light is emitted; attaching at least one retroreflector to the substrate, the retroreflector assembly including a proximal surface, a distal surface, and a retroreflective portion arranged between proximal surface and the distal surface, the proximal surface being adjacent to the substrate and the distal surface being spaced away from the substrate; and positioning the distal surface from the substrate by a distance that is less than or equal to a distance of the outer primary light emitting surface to the substrate.

In one embodiment, the method includes reflecting extraneous light emitted through a surface other than the outer primary light emitting surface back toward the light emitting device.

In one embodiment, the reflected light is directed back onto the at least one light emitting device.

In one embodiment, the method includes selectively controlling a color of light redirected by the at least one retroreflector back onto light emitting device to enhance optical spectrum performance of the light emitting device.

An advantage of the present invention is the provision of a method and apparatus using a retroreflector element to improve the optical properties of an LED.

Another advantage of the present invention is the provision of a method and apparatus using a retroreflector element to eliminate a halo effect of the output light without increasing light beam diameter.

Still another advantage of the present invention is the provision of a method and apparatus that uses a retroreflector element to increase the beam lumens per watt of an LED luminaire.

Still another advantage of the present invention is the provision of a method and apparatus that uses a retroreflector element to prevent cross-contamination with light produced by closely adjacent LEDs.

Still another advantage of the present invention is the provision of a method and apparatus that uses a retroreflector element to reintroduce wasted extraneous light back into a source LED for the purpose of a chromaticity shift.

Yet another advantage of the present invention is the provision of a method and apparatus that uses a retroreflector element to enhance the color rendering index (CRI) or individual color rendering values of an LED light source.

These and other advantages will become apparent from the following description of illustrated embodiments taken together with the accompanying drawings and the appended claims.

BRIEF DESCRIPTION OF THE DRAWINGS

The invention may take physical form in certain parts and arrangement of parts, an embodiment of which will be described in detail in the specification and illustrated in the accompanying drawings which form a part hereof, and wherein.

DETAILED DESCRIPTION OF THE INVENTION

Figure 1:
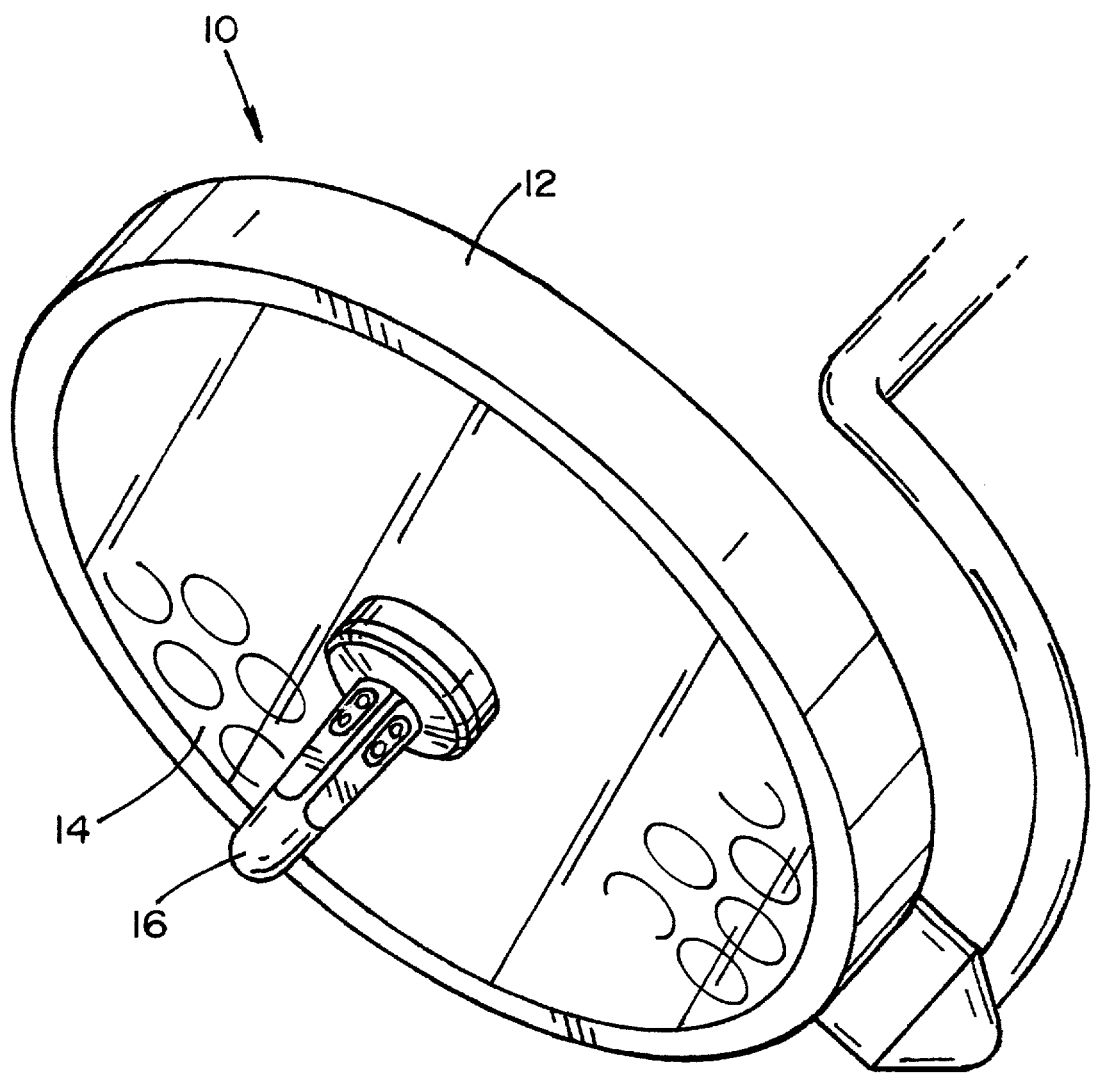
FIG. 1 is a perspective view of an exemplary surgical lighthead that includes a retroreflector assembly according to an embodiment of the present invention.

The present invention provides a lighting apparatus and method of producing a lighting apparatus that produces enhanced optical output relative to a conventional lighting apparatus. A novel lighting apparatus in accordance with the invention includes a substrate, and at least one light emitting device attached to the substrate. The light emitting device includes an outer primary light emitting surface through which substantially all light is emitted. The substrate may be a planar substrate, such as a circuit board or the like.

The light emitting device may comprise an LED package or the like. As used herein, an LED package refers to an LED device that includes an LED as well as one or more additional components other than the LED, such as one or more materials for dissipating heat, making electrical connections, providing structural rigidity, etc. The term LED package includes LED devices having minimal packaging, such as chip scale packages.

Light generated by the light emitting device is emitted substantially in a first direction (e.g., a forward-facing direction of the light emitting device). As used herein, to emit light substantially in a forward-facing direction is defined as at least 80 percent of light emitted from the light emitting device is in the forward-facing direction. The forward-facing direction can span an arc of 160 degrees with respect to the absolute forward facing direction (i.e., between 10 degrees and 170 degrees in the forward-facing direction, where 90 degrees represents absolute forward-facing direction).

As discussed above, for various reasons not all light emitted from the light emitting device may be emitted in the first (forward-facing) direction and, as a result, some extraneous light may be emitted in a second direction different from the forward-facing direction (e.g., up to 20 percent of the light may be emitted laterally and/or in a rearward-direction relative to the forward-facing direction). The second direction may extend generally rearward (i.e., between 190 and 350 degrees, where 90 degrees represents the absolute forward facing direction) and/or may extend laterally from the absolute forward-facing direction, e.g., the second direction may be generally orthogonal to the absolute forward facing direction (i.e., between 170 degrees and 190 degrees and between 10 degrees and 350 degrees, where 90 degrees represents the absolute forward-facing direction).

To prevent such extraneous light from interfering with other light emitting devices of the lighting apparatus, a retroreflector assembly is directly or indirectly attached to the substrate (e.g., the retroreflector assembly may be attached to another component, and that component may be attached to the substrate). The retroreflector assembly includes a proximal surface arranged adjacent to the substrate, a distal surface spaced away from the substrate, and a retroreflective portion arranged between the proximal surface and the distal surface. In one embodiment, the retroreflective portion spans the entire distance between the proximal and distal surfaces. The retroreflector assembly is configured such that a distance from the distal surface to the substrate is less than or equal to a distance from the outer primary light emitting surface of the light emitting device to the substrate. In one embodiment the distal surface is coplanar with the outer primary light emitting surface, and in another embodiment the distal surface is below the outer primary light emitting surface, i.e., the distal surface is closer to the substrate than the primary light emitting surface.

The retroreflector assembly is operative to reflect the extraneous light in a direction opposite the second direction and back toward the light emitting device, thereby preventing the extraneous light from interfering with other light emitting devices on the substrate. In one embodiment, the light emitting device and a retroreflector of the retroreflector assembly are closely coupled (i.e., no optically significant components are arranged between light emitting device and the retroreflector assembly) such that the extraneous light is unaltered and/or unimpeded over the optical path between an output surface of the light emitting device and a reflecting surface of the retroreflector assembly. As used herein, substantially unaltered is defined as the intensity of the light does not decrease by more than 1% and direction does not change by more than 1 degree when the light first encounters and then is transmitted through the material.

Figure 2:
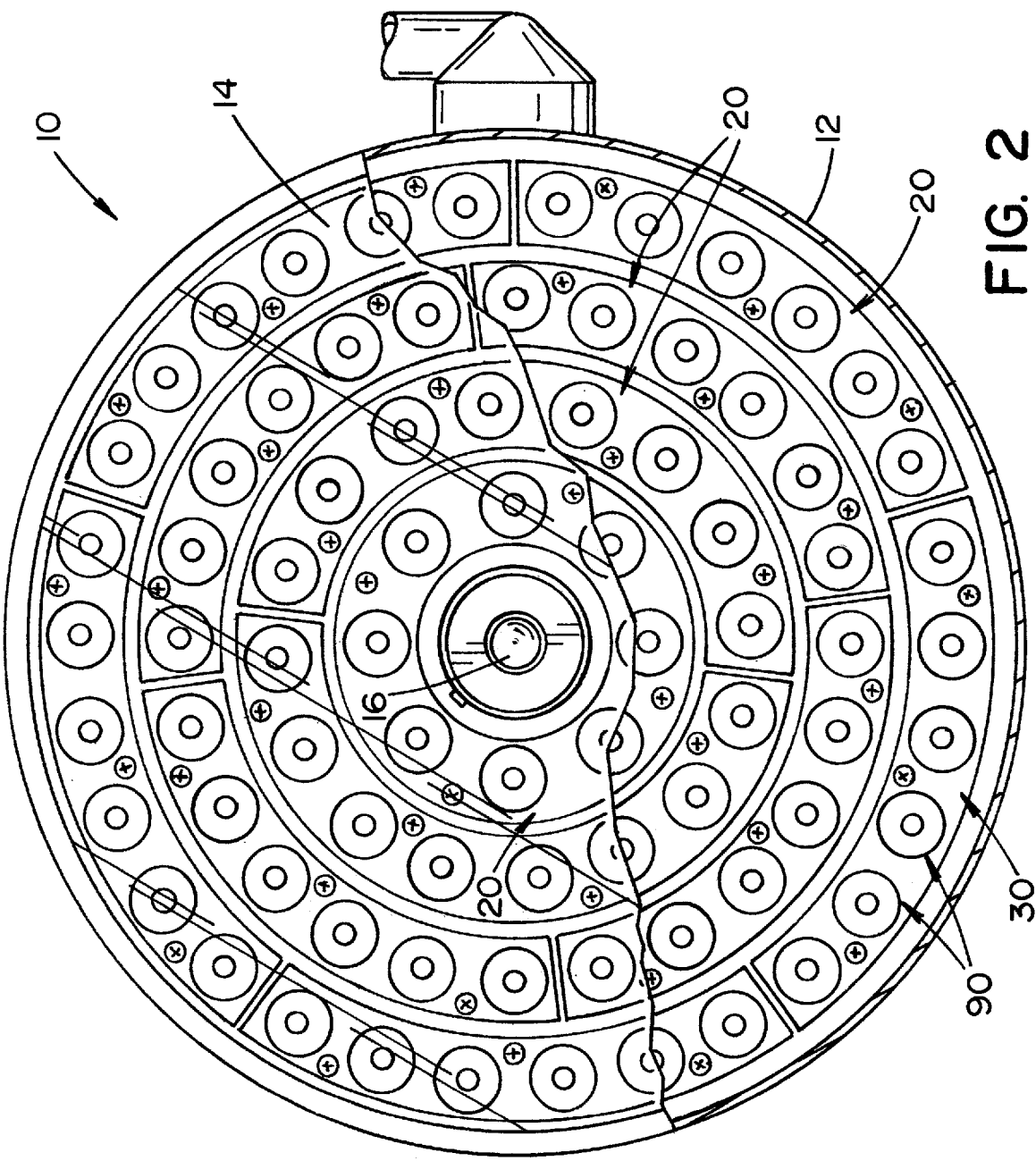
FIG. 2 is a front plan view of the surgical lighthead shown in FIG. 1, wherein a plurality of lighting modules are shown within a housing.

Referring now to the drawings wherein the showings are for the purposes of illustrating an embodiment of the invention only and not for the purposes of limiting same, FIGS. 1 and 2 show an exemplary surgical lighthead 10 that includes a retroreflector assembly according to an embodiment of the present invention. Lighthead 10 is generally comprised of a housing 12, a handle 16 which may be detachable from housing 12, and a plurality of lighting modules 20 that are located within housing 12. Housing 12 includes a transparent cover 14. It should be understood that lighthead 10 illustrated and described herein is shown only as an example embodiment, and that it is contemplated that the retroreflector assembly of the present invention may be incorporated into lightheads of alternative configurations.

Figure 3:
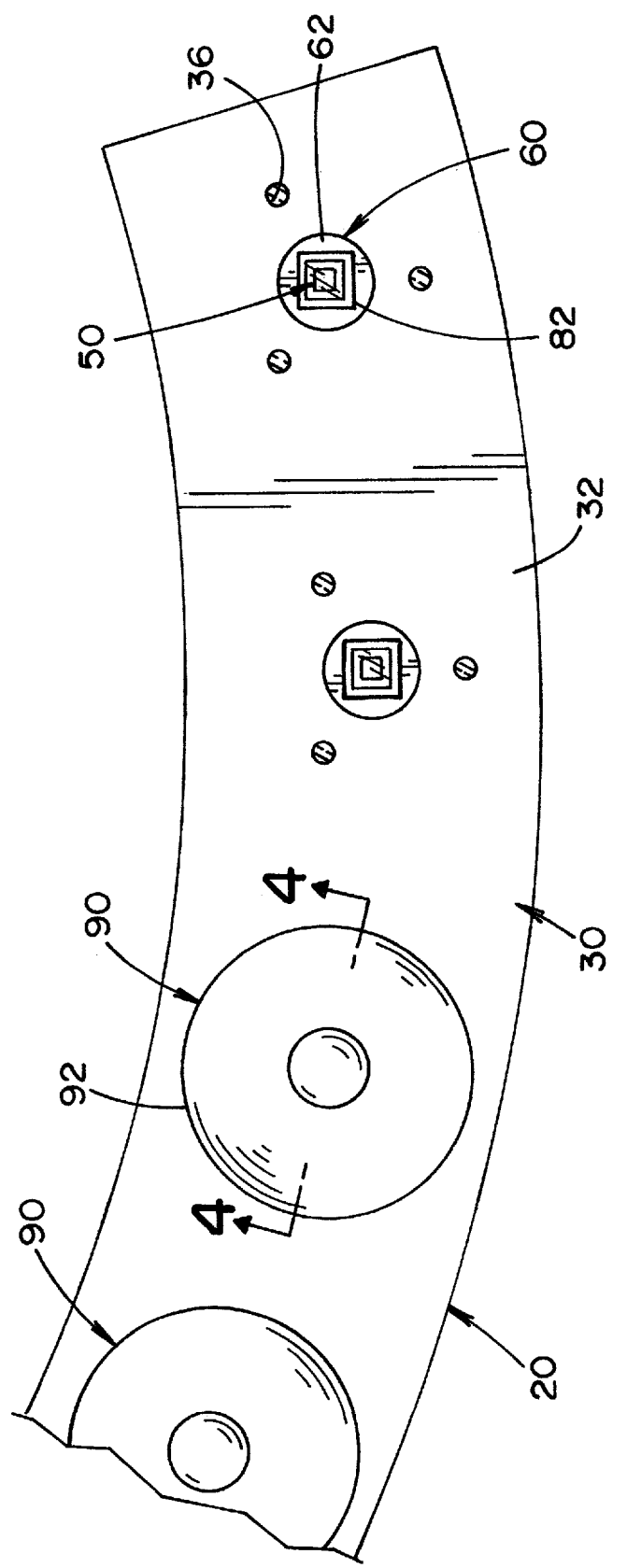
FIG. 3 is a top plan view of a portion of a circuit board substrate of the lighting module, wherein an embodiment of the retroreflector assembly of the present invention is shown.
Figure 4:
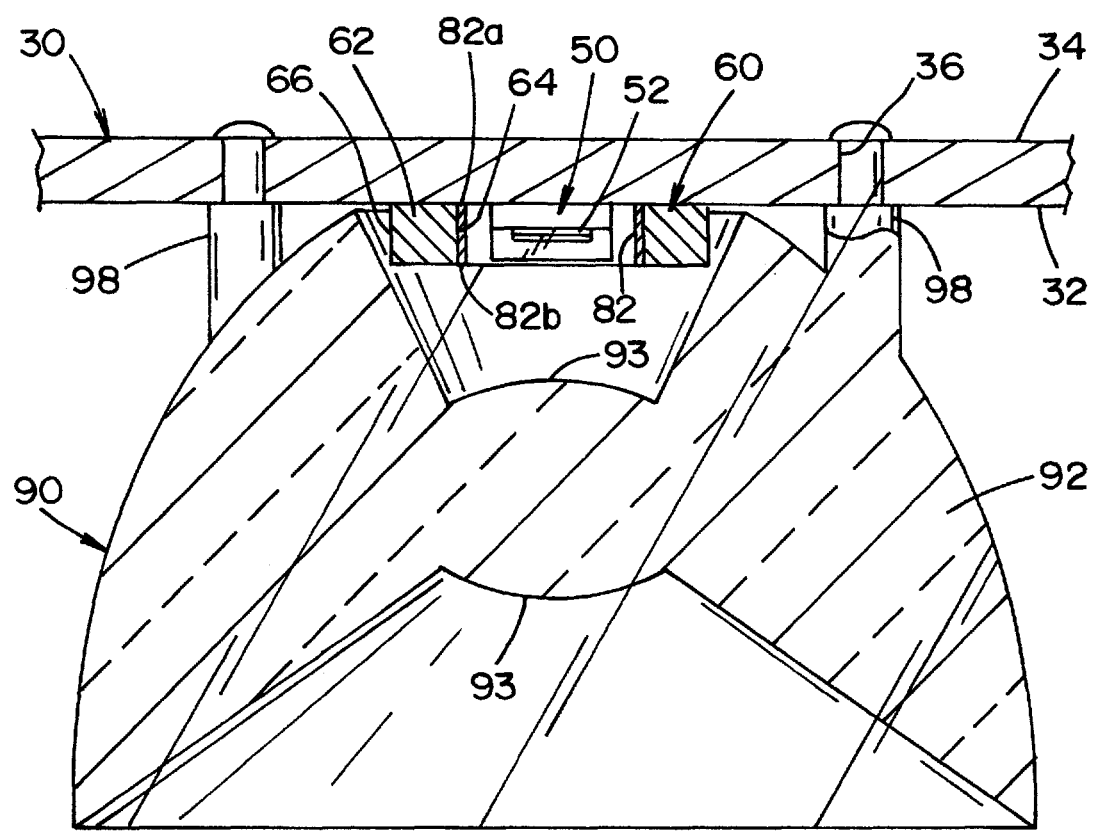
FIG. 4 is a cross-sectional view taken along lines 4-4 of FIG. 3.

Referring now to FIGS. 3 and 4, there is shown a portion of a lighting module 20 according to an illustrated embodiment. Lighting module 20 is generally comprised of a circuit board substrate 30, a light emitting device such as, for example, an LED package 50, a retroreflector assembly 60, and an optical component 90, such as a collimator or other optical device arranged over the LED package 50. As can be seen, in the exemplary embodiment the LED package 50 and the collimator 90 are attached to the substrate 30, where the LED package 50 is arranged between the substrate 30 and the collimator 90. The collimator 90 is operative to collimate light emitted by the LED package 50 in the forward-facing direction of the LED package 50.

Circuit board substrate 30 has a front surface 32 (FIG. 3) and a rear surface 34 (FIGS. 3 and 4). A plurality of holes 36 are formed in circuit board substrate 30 for mounting collimator 90. With additional reference to FIG. 5, circuit board substrate 30 also includes conductive trace wires 38 for electrical connection of LED package 50 to power and control systems (not shown).

Figure 6:
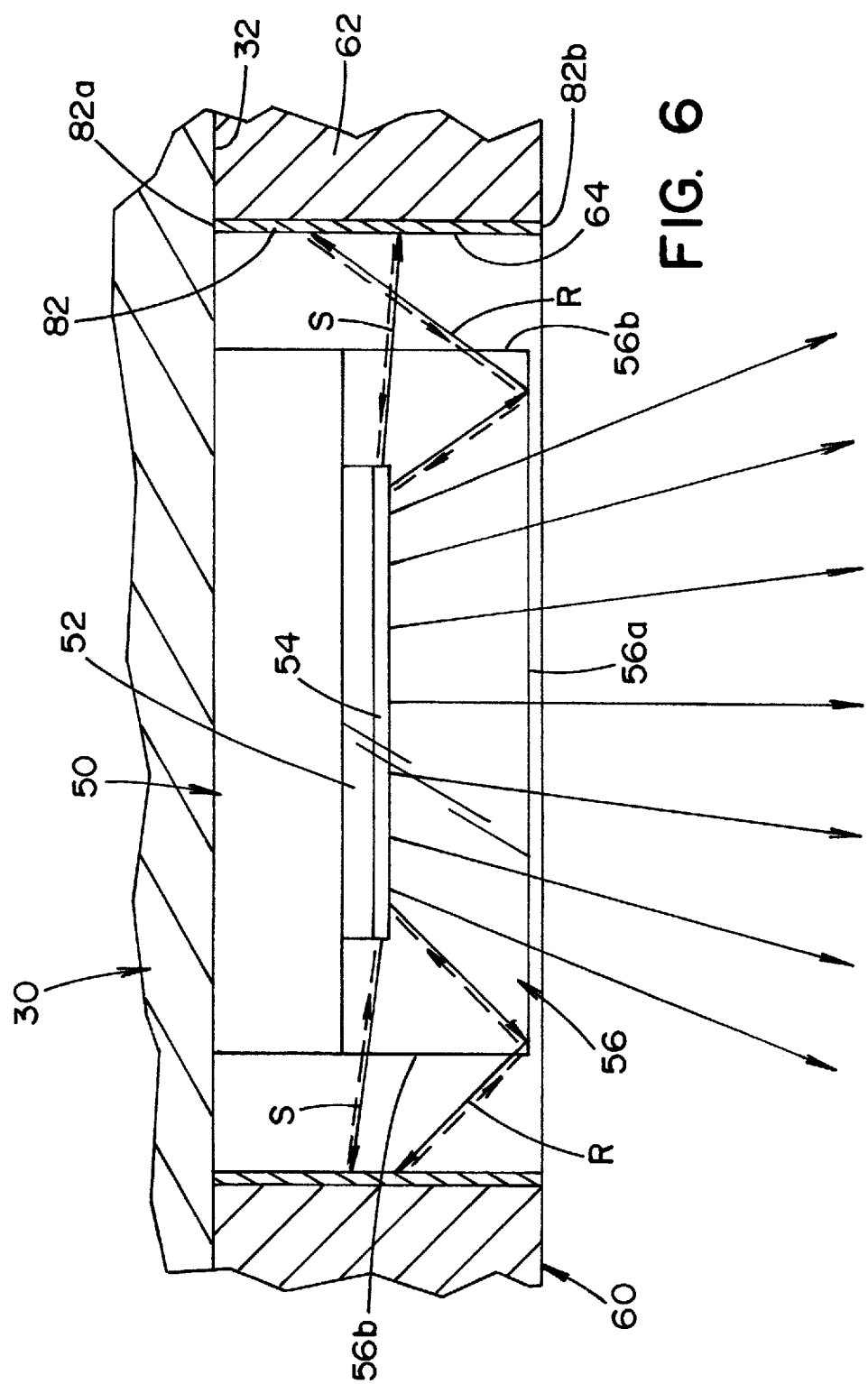
FIG. 6 is a cross-sectional view of an LED mounted to a circuit board substrate and the retroreflector assembly of the present invention.

Referring briefly to FIG. 6, LED package 50 is comprised of an LED 52 (e.g., a blue LED), a luminous source, such as a yellow phosphor layer 54 for producing white light, and an encapsulant 56 (e.g., silicone, epoxy, glass, or plastic) arranged over the LED. The encapsulant can define a primary light emitting surface 56a that emits light in substantially the first direction (e.g., the forward-facing direction), and a secondary light emitting surface 56b that emits extraneous light in the second direction (e.g., lateral direction S or rearward direction R). In some LED packages (not shown) phosphor may be distributed throughout the encapsulant. Examples of LED packages which may emit extraneous lateral side and rearward light include flat, non-domed, high power packages, such as Cree® XQ-E high intensity silicon carbide type packages. Such types of LED packages may direct 5% to 20% of the total light of the LED toward the lateral side and rearward directions.

Figure 5:
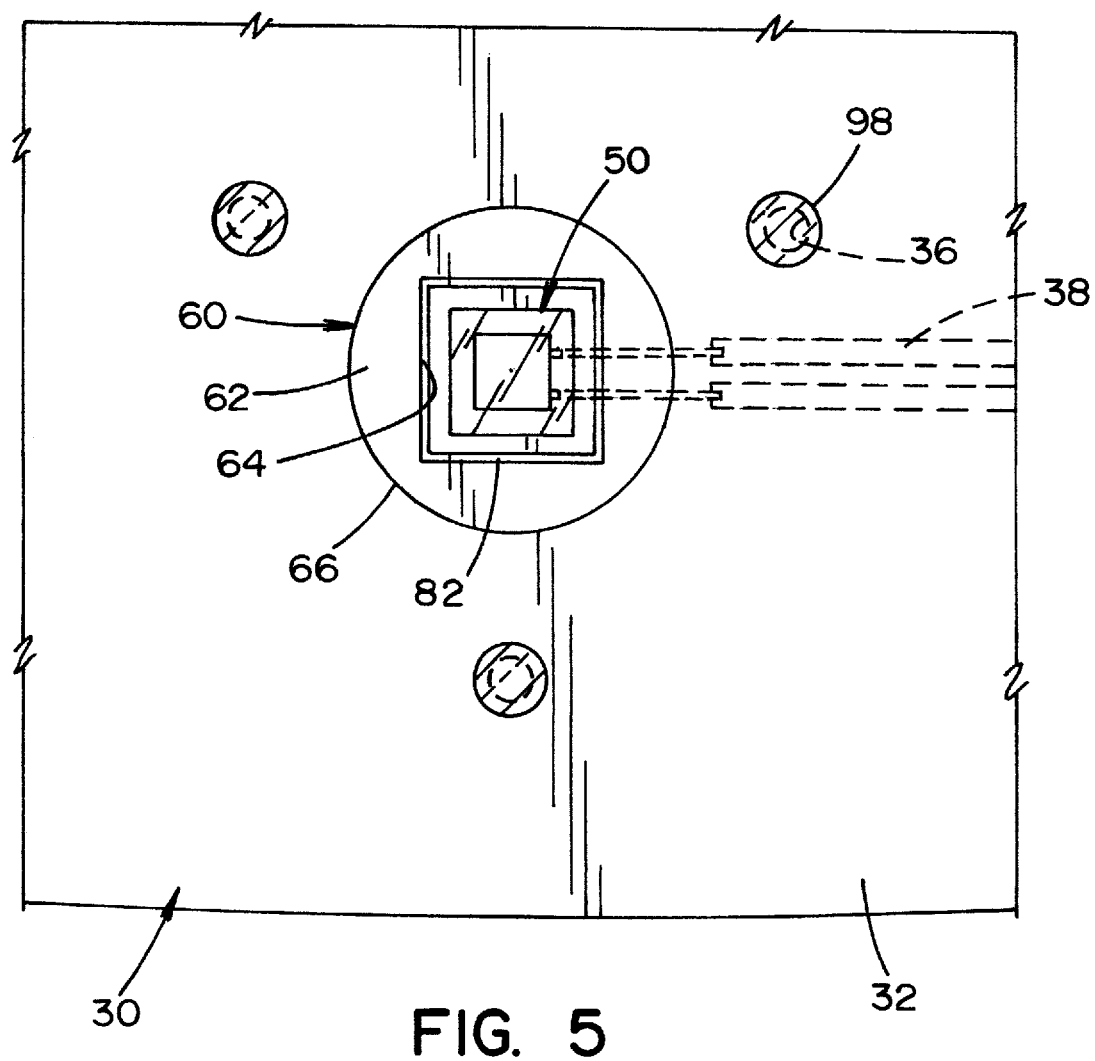
FIG. 5 is an enlarged plan view of the retroreflector assembly.

Retroreflector assembly 60, best shown in FIGS. 4 and 5, is comprised of a support member 62 having an inner surface 64 and an outer surface 66, and a retroreflector element 82 arranged on the inner surface 64, the retroreflector element 82 having a proximal surface 82a adjacent to the substrate 30 and a distal surface 82b spaced apart from the substrate 30. In the exemplary embodiment, a reflecting surface of the retroreflector element 82 is arranged parallel to the secondary light emitting surface 56b along lateral sides of the primary light emitting surface 56a. Support member 62 may be comprised of a high temperature plastic or glass. In the illustrated embodiment, outer surface 66 forms a cylindrical-shaped surface, while inner surface 64 forms a square-shaped surface. The inner surface 64 may be formed from a plurality of walls that define a volume, where the LED package 50 is arranged within the volume.

Retroreflector element 82 is mounted to inner surface 64, and may take various forms, including, but not limited to, a colored or black ball retroreflector (e.g., microspheres deposited onto an adhesive-backed tape or microspheres deposited on a painted plastic surface), and a corner cube retroreflector. Retroreflector element 82 may span part or all of the area between the proximal surface 82*a* and distal surface 82*b*. It should be appreciated that a retroreflector element 82 is a device or surface that reflects light back to its source with a minimum of scattering. In a retroreflector, an electromagnetic wavefront is reflected back along a vector that is parallel to but opposite in direction from the wave's source. The retroreflector element 82 is preferably placed as close as possible to the secondary light emitting surface 56*b* of the package 50. In one embodiment, the retroreflector element 82 is arranged realtive to the LED package 50 such that a distance between the retroreflector element 82 and the secondary light emitting surface 56*b* is less than two times the height of the LED package 50 (the height being defined as the distance from the outer primary light emitting surface 56*a* to the substrate 30).

In the illustrated embodiment, retroreflector element 82 takes the form of an adhesive-backed tape having microspheres applied thereto (e.g., a retroreflector tape). The retroreflector tape is applied to inner surface 64 of support member 62 such that the microspheres face towards LED package 50. In one embodiment, the retroreflector tape is applied to all four portions of the square-shaped inner surface 64 that surround LED package 50. In accordance with an alternative embodiment of the present invention, an optical component holder proximate to the LED package 50 or the surface of a circuit board substrate 30 may include a retroreflector element 82.

As indicated above, retroreflector element 82 may include a colored feature (e.g., a colored microsphere) to filter certain wavelengths of light. It is also contemplated that retroreflector element 82 may include a colored filter (i.e., filters of reflective color selection or color transmission, such as an acetate filter available from LEE Filters) to selectively control the color of reflected light through wavelength filtering. Filtering the light reflected by retroreflector element 82 can enhance the spectrum of the light emitted by LED package 50. In one embodiment, the colored filter is attached to the retroreflector surface as a coating or film. However, the colored filter may be placed anywhere in the optical path between the LED package 50 and the retroreflector element 82.

Collimator 90 typically takes the form of an optical element with a total internal reflection (TIR) portion 92 and a refractive lens portion 93 for providing collimating light and a plurality of mounting legs 98. Collimator 90 is mounted over LED package 50 by insertion of mounting legs 98 into holes 36 of circuit board substrate 30, as best seen in FIG. 4. Collimator 90 may have a shape that differs from the collimator illustrated in FIG. 4.

Operation of the retroreflector assembly of the present invention will now be described with reference to FIG. 6. In general, light that is emitted by LED package 50 to the lateral sides (labeled as light beams S) and rearwards (labeled as light beams R) is redirected by retroreflector elements 82 back onto LED package 50. Thereafter, this redirected light is diffusely reflected or absorbed and re-emitted from LED package 50 with an angular distribution similar to the initial light emission. The foregoing process improves the optical properties of LED package 50. In this regard, a halo effect of the output light is eliminated without increasing the light beam diameter, beam lumens per watt is increased, and cross-contamination with the light produced by proximate LEDs is prevented.

It should be noted that conversion of narrow band blue light emitted by the LED package 50 to broad band white light occurs only once, ideally, on the first pass thru the phosphor layer. If blue light escapes the LED package, it may be converted to white light in a neighboring LED package. Retroreflected light may be comprised of both blue and white light. If the blue light strikes the phosphor, some portion may be absorbed and reemitted as white light. If white light strikes the phosphor it will be diffusely reflected.

In an embodiment of the present invention where a wavelength filter (e.g., filters of reflective color selection or color transmission) is used, the color of the light redirected by retroreflector element 82 back onto LED package 50 is selectively controlled to enhance the optical spectrum performance of LED package 50. The wavelength filter may take the form of a colored acetate filter or a colored retroreflective surface. According to one embodiment of the present invention, retroreflector elements 82 are colored to enhance the spectral properties of the light.

The redirection of the light emitted to the lateral sides (light beams S) and rearward (light beams R) back into LED package 50, and in some cases, back onto the luminous source (i.e., phosphor layer 54) results in improvements to LED efficacy or improvements to the LED's spectrum, thereby increasing the general color rendering index, CRI, or a special color rendering index, such as R9, which is the color rendering index for deep, saturated red.

Other modifications and alterations will occur to others upon their reading and understanding of the specification. It is intended that all such modifications and alterations be included insofar as they come within the scope of the invention as claimed or the equivalents thereof.

Having described the invention, the following is claimed:

1. A light emitting apparatus, comprising:
a circuit board substrate comprising conductive traces;
at least one light emitting device arranged on the circuit board substrate and electrically connected to the conductive traces, the at least one light emitting device including an outer primary light emitting surface through which substantially all light is emitted;
an optical component arranged on the circuit board and over the at least one light emitting device, the at least one light emitting device disposed between the circuit board substrate and the optical component, wherein light emitted from the outer primary light emitting surface impinges a surface of the optical component, and
a retroreflector assembly arranged on the circuit board substrate, the retroreflector assembly including a proximal surface adjacent to the circuit board substrate, a distal surface spaced away from the circuit board substrate, and a retroreflective portion arranged between the proximal surface and the distal surface,
wherein a distance from the distal surface to the circuit board substrate is less than or equal to a distance from the outer primary light emitting surface to the circuit board substrate.

2. The light emitting apparatus according to claim 1, wherein the retroreflector assembly is arranged along lateral sides of the outer primary light emitting surface.

3. The light emitting apparatus according to claim 1, wherein the distal surface is coplanar with the outer primary light emitting surface.

4. The light emitting apparatus according to claim 1, wherein at least some extraneous light is emitted through a surface of the light emitting device other than the outer primary light emitting surface, and the retroreflector assembly is configured to reflect the at least some extraneous light back toward the light emitting device.

5. The light emitting apparatus according to claim 1, wherein the optical component comprises an optical component having at least one of refractive or reflective portions arranged over the at least one light emitting device, the optical component configured to collimate light emitted by the outer primary light emitting surface.

6. The light emitting apparatus according to claim 1, wherein the light emitting device comprises a light emitting diode (LED).

7. The light emitting apparatus according to claim 1, wherein the retroreflective portion spans from the distal surface to the proximal surface.

8. The light emitting apparatus according to claim 1, wherein the retroreflective portion of the retroreflector assembly is arranged parallel to a lateral side of the light emitting device.

9. The light emitting apparatus according to claim 1, wherein the retroreflector assembly comprises a support member having an inner surface, and a retroreflector arranged on the inner surface.

10. The light emitting apparatus according to claim 1, wherein the circuit board substrate comprises a planar surface.

11. The light emitting apparatus according to claim 1, further comprising a colored filter configured to selectively control a color of reflected light to enhance a spectrum of the light emitted by the light emitting device.

12. The light emitting apparatus according to claim 1, wherein the at least one light emitting device and a retroreflector of the retroreflector assembly are closely coupled.

13. A surgical light head, comprising:
a housing; and
the light emitting apparatus according to claim 1 arranged within the housing.

14. The light emitting apparatus according to claim 1, wherein the retroreflective portion spans the entire distance between the proximal surface and the distal surface.

15. The light emitting apparatus according to claim 1, wherein the retroreflective portion is operative to reflect light emitted by the at least one light emitting device in an opposite direction back toward the at least one light emitting device.

16. The light emitting apparatus according to claim 1, wherein the retroreflector assembly is operative to redirect light emitted from lateral sides of the at least one light emitting device back toward the at least one light emitting device along a direction parallel to and opposite in direction of the light emitted from the lateral sides of the at least one light emitting device.

17. The light emitting apparatus according to claim 1, wherein the outer primary light emitting surface comprises a planar surface.

18. The light emitting apparatus according to claim 4, wherein the reflected light is directed back onto the at least one light emitting device.

19. The light emitting apparatus according to claim 4, wherein substantially all light is emitted in a forward-facing direction of the light emitting apparatus, and at least some light is emitted in at least one of i) a lateral direction relative to the forward-facing direction or ii) a reverse-facing direction relative to the forward-facing direction.

20. The light emitting apparatus according to claim 4, wherein at least some light is emitted in a direction generally orthogonal to the forward-facing direction or a direction generally opposite the forward-facing direction.

21. The light emitting apparatus according to claim 4, wherein an intensity of the extraneous light is substantially unaltered over an optical path between the at least one light emitting device and the retroreflector assembly.

22. The light emitting apparatus according to claim 5, wherein the retroreflector assembly is indirectly attached to the circuit board substrate.

23. The light emitting apparatus according to claim 6, wherein the light emitting device comprises a phosphor layer arranged over an output surface of the LED.

24. The light emitting apparatus according to claim 9, wherein the inner surface comprises a plurality of walls that define a volume, and the light emitting device is arranged within the volume.

25. The surgical lighthead according to claim 13, further comprising a handle for positioning the lighthead, the handle attached to the housing.

26. The light emitting apparatus according to claim 22, wherein the collimator is directly attached to the circuit board substrate and the retroreflector assembly is attached to the collimator.

27. The light emitting apparatus according to claim 23, wherein light reflected by the retroreflector assembly comprises blue light and white light, the blue light being absorbed by the phosphor layer and reemitted as white light, and white light being diffusely reflected by the phosphor layer.

28. The light emitting apparatus according to claim 23, wherein the light emitting device comprises an encapsulant arranged over the LED, the encapsulant defining the outer primary light emitting surface and a secondary light emitting surface that emits the extraneous light.

29. A method for improving optical illumination properties of a lighting apparatus, comprising:
arranging a light emitting device on a circuit board substrate having conductive traces;
electrically connecting the light emitting device to the conductive traces, wherein the light emitting device has an outer primary light emitting surface through which substantially all light is emitted;
arranging at least one retroreflector assembly on the circuit board substrate, the retroreflector assembly including a proximal surface, a distal surface, and a retroreflective portion arranged between proximal surface and the distal surface, the proximal surface being adjacent to the circuit board substrate and the distal surface being spaced away from the circuit board substrate;
positioning the distal surface from the circuit board substrate a distance that is less than or equal to a distance of the outer primary light emitting surface to the circuit board substrate; and
arranging an optical component on the circuit board substrate and over the light emitting device, the light emitting device disposed between the circuit board substrate and the optical component, wherein light emitted from the outer primary light emitting surface impinges a surface of the optical component.

30. The method according to claim 29, further comprising reflecting extraneous light emitted through a surface other than the outer primary light emitting surface back toward the light emitting device.

31. The method according to claim 29, wherein the reflected light is directed back onto the at least one light emitting device.

32. The method according to claim 29, further comprising selectively controlling a color of light redirected by the at least one retroreflector back onto light emitting device to enhance optical spectrum performance of the light emitting device.

* * * * *